US00PP10421P

United States Patent [19]

Lemon

[11] Patent Number: Plant 10,421

[45] Date of Patent: May 26, 1998

[54] VARIETY OF GERANIUM PLANT NAMED 'PEACHES'

[75] Inventor: David Lemon, Lompoc, Calif.

[73] Assignee: John Bodger & Sons Company, So. El Monte, Calif.

[21] Appl. No.: 821,261

[22] Filed: Mar. 20, 1997

Related U.S. Application Data

[63] Continuation of Ser. No. 571,169, Dec. 12, 1995, abandoned.

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 5,374 12/1984 Schumann ..... Plt./87.12

*Primary Examiner*—Howard J. Locker
*Attorney, Agent, or Firm*—Fulwider Patton Lee Utecht, LLP

[57] ABSTRACT

The cultivar is characterized by the distinctive clear salmon color of the bloom over medium green foliage. Its quick rooting time and continuous flowering provides for superb cuttings and for quick recovery of the bloom following wet weather conditions. The blooms are heat tolerant, and an abundant amount of cuttings may be obtained from a single plant.

1 Drawing Sheet

This application is a continuation of application Ser. No. 08/571,169 filed on Dec. 12, 1995 (abandoned).

BACKGROUND OF THE NEW PLANT

The present invention comprises a new and distinct cultivar of *Pelargonium×hortorum* known by the varietal name Peaches (Oglevee No. 1339, Bodger No. 1GM 172-10). The new variety was discovered in a seletive breeding program by David Lemon at Bodger Seeds, Ltd., Lompoc, Calif. The new variety is a selection from the crossing of Schone Helena (U.S. Plant Pat. No. 5,374) which is a salmon rose color having a semi-doubled flower crossed with Eclipse Light Salmon (unpatented) which can be distinguished from the claimed cultivar by its light salmon color and dark green leaves.

The new cultivar was first asexually reproduced by cuttings at Oglevee Ltd., Connellsville, Pa. , and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected form asexual reproduction carried out by Oglevee Ltd. in Connellsville, Pa. The plant histories were taken on rooted cuttings believed to have been potted on approximately Feb. 18, 1995 and flowering on approximately Apr. 1, 1995 under full light and greenhouse, and colorings were taken indoors under 200–220 foot candles of fluorescent cool white light using The R.H.S. Colour Chart of The Royal Horticultural Society of London.

The Plant

Classification:
- *Botanical.*—*Pelargonium×hortorum.*

Form: Semi-dwarf mound.
- *Height.*—17.0–19.0 cm above the media surface.
- *Growth.*—Free and easy flowering; free basal branching.
- *Strength.*—Free standing. Foliage: Stalked leaf attachment; no prominent zone present although some zoning having a similar hue to the rest of the leaf may occur, it is not readily apparent.

Leaves:
- *Size.*—8.5–11.0 cm across; fully expanded leaf.
- *Shape.*—Reinform; cordare base.
- *Margin.*—Crenate.
- *Texture.*—Pubescent; slightly reflective.
- *Color.*—Top: Green group 137B; Zone: Not present. Bottom: Green group 137D.
- *Ribs and veins.*—Palmate venation: Color: Yellow/green group 146C.

Petioles:
- *Length.*—6.0–7.5 cm.
- *Color.*—Yellow/green group 146C.

Stem:
- *Color.*—Yellow/green group 146C.
- *Internodes.*—1.5–3.0 cm in length.

The Bud

Shape: Upright; hemispherical cluster.
Size: 2.5–3.5 cm across.

Inflorescence

Blooming habit: Semi-double; continuous blooming; slow to shatter.
Size: 8.5–10.0 cm across; fully open bloom.
Borne: Umbel; florets on pedicel; pedicel on peduncle; 6.0–10.0 cm above foliage.

Florets:

*Closed.*—Bud size: 1.0–1.5 cm in length, 0.6–0.8 cm in width; elliptical.

*Open.*—Form—Flat to slightly cupped; petaloids present; 22 florets per inflorescense. Color—Top: Red Group 38B; Bottom: Red Group 38C; Eye: not present. Petals—8–12 in number; single, not united; margin entire; obovate; smooth; flat to slightly cupped. Size—3.0–4.0 cm across when fully open. Texture and appearance.—Smooth and satiny. Appearance from a distance is a rich medium salmon peach bloom above medium green foliage.

Petaloids:

*Quantity.*—1–5 in number.

*Shape.*—Flat, twisted; some with pollen attached (the structure may not change completely to a full petaloid form and may retain some anther characteristics).

*Color.*—Top: Red Group 38C; Bottom: Red Group 38D.

Pedicel:

*Length.*—2.5–3.5 cm.

*Color.*—Yellow-green group 146C.

Peduncle: Arises from the node opposite the leaf petiole.

*Length.*—14.5–16.5 cm in length.

*Color.*—Yellow-green group 146C.

Persistence:

*Disease resistance.*—Not known.

*Lasting quality.*—Slow to shatter.

Reproductive organs

Stamens:

*Anthers.*—2.0–3.0 mm in length.

*Filaments.*—7.0–9.0 mm in length; white.

*Pollen.*—Golden brown.

Pistils:

*Number.*—One.

*Length.*—7.0–8.0 mm.

*Stigma.*—5–6 parted; Color: red-purple group 60C.

*Style.*—3.0–4.0 mm in length; Color: Red-purple group 60C.

Ovaries: Pubescent; light green in color; 4.0–5.0 mm in length.

Fruit: None.

General Characteristics

Peaches presents an attractive new color to the Geranium market. The pure salmon peach color of the bloom above medium green foliage creates a distinctive, eye catching appearance. Peaches provides an abundant amount of cuttings which are quick to root. Finishing this variety as a pot plant can be done very quickly and economically with many plants fitting on one bench without sacrificing outdoor performance. Peaches is extremely heat tolerant and is quick to recover after wet weather with a speedy replacement of bloom. Given all these positive properties, this variety should please both the grower and the gardener.

I claim:

1. A new and distinct variety of Geranium plant, substantially as shown and described.

* * * * *

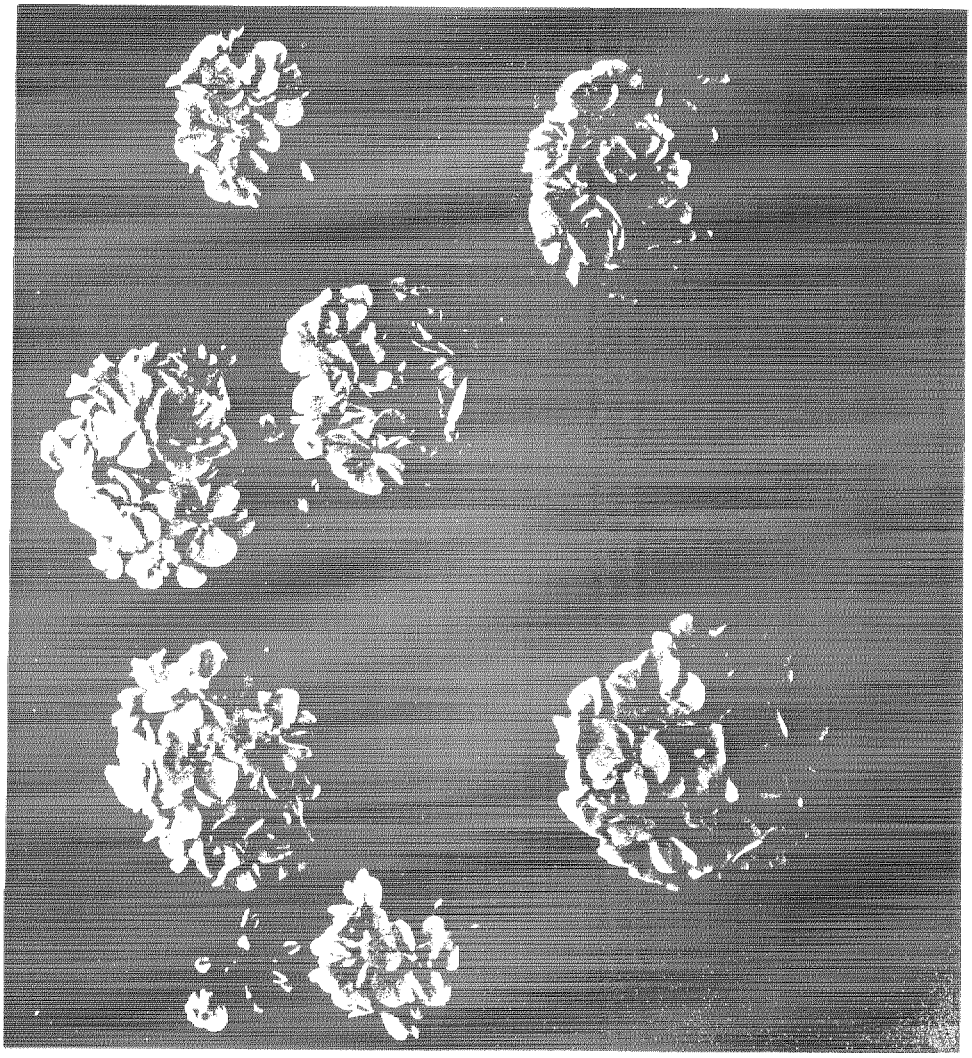

PLT-328 SR 1
C5203 OR PP 010,421
U.S. Patent May 26, 1998 Plant 10,421